United States Patent [19]

Guenther et al.

[11] Patent Number: 4,826,318
[45] Date of Patent: May 2, 1989

[54] APPARATUS FOR ELECTROTHERMAL ATOMIZATION

[75] Inventors: Horst Guenther; Wolfgang Foest, both of Berlin; Klaus Eichardt, Jena, all of German Democratic Rep.

[73] Assignee: Jenoptik Jena GmbH, Jena, German Democratic Rep.

[21] Appl. No.: 74,746

[22] Filed: Jul. 17, 1987

[30] Foreign Application Priority Data

Sep. 1, 1986 [DD] German Democratic Rep. .................................. 2940163

[51] Int. Cl.⁴ ............................................. G01N 21/74
[52] U.S. Cl. .................................................... 356/312
[58] Field of Search ........................................ 356/312

[56] References Cited

U.S. PATENT DOCUMENTS

| 4,303,339 | 12/1981 | Gläser et al. | 356/312 X |
| 4,407,582 | 10/1983 | Woodriff | 356/312 |
| 4,657,389 | 4/1987 | Littlejohn | 356/312 |

FOREIGN PATENT DOCUMENTS 2023336 12/1971 Fed. Rep. of Germany ...... 356/312

Primary Examiner—Vincent P. McGraw
Attorney, Agent, or Firm—Jordan and Hamburg

[57] ABSTRACT

In an apparatus for electrothermal atomization, which can be used for flameless atomic absorption spectroscopy as well as for flameless atomic emission spectroscopy, a platform positioned in a graphite tube is divided into two functional axially adjacent. One of the regions serves as the holding part and the other serves as the sample-carrying part. The holding part is mounted in the area of one of the tube ends and the sample-carrying part protrudes unsupported into the interior of the tube.

7 Claims, 2 Drawing Sheets

APPARATUS FOR ELECTROTHERMAL ATOMIZATION

The invention relates to an apparatus for the electrothermal atomization of analytical samples. The apparatus can be used in flameless atomic absorption spectroscopy (AAS) and emission spectroscopy.

BACKGROUND OF THE INVENTION

In trace analysis, heating equipment, usually referred to as tubular graphite furnaces, are usually used as electrothermal atomizers. In recent years, sample carriers, which are referred to as platforms and can be introduced into the tubular graphite furnaces, have increasingly been used. To achieve as isothermal an atomization as possible, which is important especially for real sample analyses, it is necessary to provide means for preheating the gas atmosphere in the interior of the tubular graphite furnace before the vaporization and atomization of the material to be analyzed commences.

Among the variously proposed atomization apparatuses which are said to ensure isothermal conditions, such as the T cuvette, (DE OS No. 2,713,637), double-wall furnace (U.S. Pat. No. 4,407,582), graphite probe technique (DE OS No. 3,044,627, DE-OS No. 3,217,417) and the platform technique, the latter has gained acceptance on the basis of its simplicity and the problem-free metering of sample solutions.

It is disclosed in DE OS No. 2,924,123 that rectangular platforms of solid pyrographite, which are fixed in a groove that runs axially symmetrically to the tube axis, may be used in standard graphite tubes.

Furthermore, it is disclosed in DE Utility Patent No. 7,825,590 that a sample carrier may be used having an outer surface which lies against the inner wall of the cuvette.

To limit the contact between the platform and the graphite tube as much as possible, DD WP 227,523 discloses that the platform be provided with small supporting feet. It is a disadvantage of these proposed solutions that, due to the construction, the heating curent flows through the sample carriers which or the sample carriers are in direct contact with the tubular graphite furnace, so that, aside from the heat radiating from the wall of the tube, the heated platform itself contributes to a considerable extent to the vaporization and atomization. The desired delayed atomization can thus be realized only to an unsatisfactory extent.

A variation of the platform measurements is also known in which the platform is pushed from the front through a slit into the cuvette. The slit, however, is precisely in the hot zone of the furnace, so that here also the thermal conduction does not lead to an optimum delay in the platform heating in relation to the tube wall. Moreover, for reasons of space, the atomizer configuration is restricted to a rectangular cuvette geometry which is extremely expensive to manufacture.

SUMMARY OF THE INVENTION

The object of the invention is to provide an inexpensive apparatus which can be used for electrothermal atomization, which improves the analytical applicability of AAS—especially to real sample investigations, that is, to samples with a higher matrix portion.

The invention is directed to the problem of ensuring at least approximate isothermal conditions in the atomization phase, so that signal depressions do not occur even at higher matrix contents in the analytical sample.

The objective is accomplished pursuant to the invention by means of an apparatus for the eletrothermal atomization which contains a platform as the sample carrier in a graphite tube. The platform is divided into two adjacent functional areas in the axial direction. One of these functional areas serves as a holding part and the other as a sample-carrying part. The holding part is mounted essentially in the area of one of the ends of the tube and the sample-holding part protrudes unsupported into the interior of the tube.

An advantageous solution provides a broader section of a T-shaped part for the holding part and a narrower section of the T-shaped part for the sample-carrying part. The broader section is pushed into two slits lying in, plane at one end of the graphite tube so as to form a good and flush seal. The height of the slits is so dimensioned that there is a fit between the sample carrier and the graphite tube and mixing between the inner and outer gas streams is precluded. The correct positioning of the sample carrier is achieved by the axial length of the slits. Due to the flush termination of the sample carrier with the end of the graphite tube, direct cooling of the sample carrier over a cooled electrode, applied to the graphite tube, is possible. By these means, an additional, detectable time lag in the heating of the sample carrier is brought about. The temperature gradient, thereby directed from the sample-carrying part to the holding part, increases the desired delay in the atomization already achieved by the unsupported disposition of the sample-carrying part, so that with accurate positioning of the sample in the graphite tube, the atomization takes place under almost ideal, isothermal conditions. Due to the contactless introduction of the sample-carrying part into the hottest zone of the graphite tube, passage of current and the direct heating associated therewith are avoided.

In a further advantageous solution, a radially symmetrical cross member that has grooves which lie in a, plane and through which the holding part is pushed, is provided for guiding and mounting the holding part in the area of one end of the tube in the interior of said tube. A shift in the temperature maximum over the length of the graphite tube can either be counteracted by a further cross member in the area of the other end of the tube or there is a compensation due to an asymmetrically disposed sample pipetting opening. The platform is pushed sufficiently far into the graphite tube that the sample-carrying part is in the hottest zone of the tube and the holding part is in the cooler end of the tube. With this second solution, the improvement in the platform effect is similar to that achieved with the first.

Reproducible positioning of the platform in the graphite tube is realized owing to the fact that the holding part is provided with at least one stop which acts against the holding cross member. This configuration of the atomizer enables the geometrically simplest sample carrier variations to be used.

Suitable materials for the platform are pyrographite, glass carbon, coated electrographite or high-melting metals, such as Ta or W.

BRIEF FIGURE DESCRIPTION

The invention will be described in greater detail below with reference to the accompanying drawing, wherein.

DETAILED DISCLOSURE OF THE INVENTION

Figure 1:
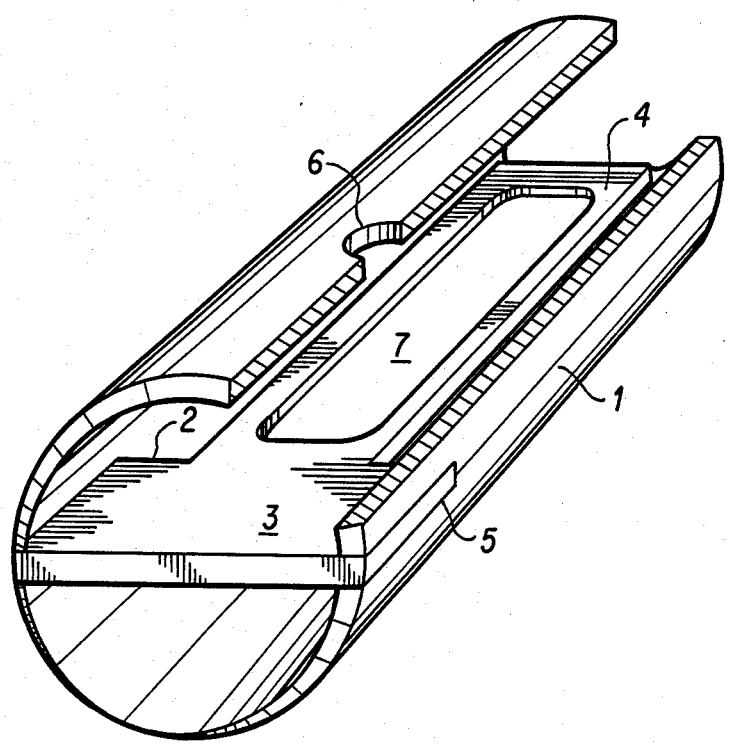
FIG. 1 shows a perspective representation of an atomizer tube with a T-shaped platform.

In FIG. 1, a sample carrier 2, in the form of a T-shaped platform, is pushed into a graphite tube 1. The sample carrier 2 has a broader holding part 3 and a narrower sample-carrying part 4. For this purpose, two slits 5, which lie in the same plane, are provided at one end of the graphite tube 1. The holding part 3 is so dimensioned that it fills the slits 5. Preferably a fit is provided for this purpose such that mixing of the internal and external streams of the inert gas is precluded. The sample-carrying part 4 protrudes freely, without contacting the graphite tube 1, into the hottest zone of this tube. A sample substance is usually introduced through a pipetting opening 6. To prevent dispersal of the sample substance, a depression 7 is provided in the sample-carrying part 4. The length of the slits 5 makes possible the reproducible positioning of the sample carrier 2 even should an exchange have become necessary, and ensures a flush termination of the holding part 3 with the end of the graphite tube 1. By such means, direct contact between the sample carrier 2 and the cooled electrode (not shown) is achieved. This has a favorable effect on the exclusive heating of the sample carrier 2 by thermal radiation.

Figure 2:
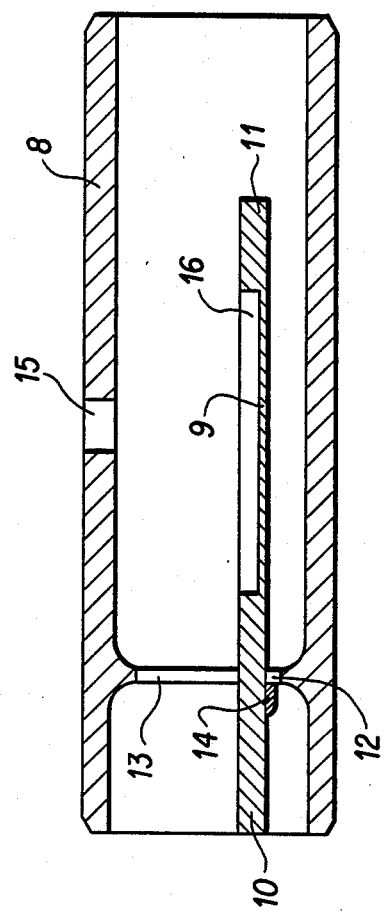
FIG. 2 shows a longitudinal section through an atomizer tube with a radial cross member to the platform holding device.
Figure 3:
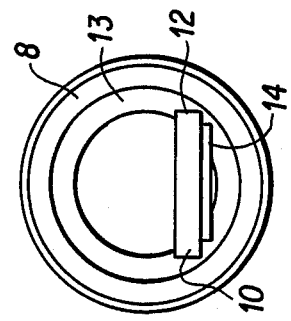
FIG. 3 shows a cross section through the atomizer tube of FIG. 2.

In a second embodiment, shown in FIG. 2, a sample carrier 9, which consists of a holding part 10 and a sample-carrying part 11 and has a rectangular shape, is pushed into a graphite tube 8 in grooves 12 of a radial cross member 13. A stop 14, functioning as a positioning aid, ensures that the sample carrier 9 can be reproducibly inserted to the same position and that the holding part 11 terminates flush with the end of the graphite tube 8. The graphite tube 8 has a pipetting opening 15 and the sample carrier 9 has a depression 16 for holding the sample.

Grooves to prevent transfer of heat can be formed between the sample-carrying parts and the holding parts of both solutions, so that only a narrow cross member remains as the connection between the two functional areas.

We claim:

1. In an apparatus for electrothermal atomization comprising a platform serving as a sample carrier and a graphite tube in which said platform is mounted, the improvement wherein the platform is divided into two functional end regions which are adjacent one another in the axial direction, one of said regions comprising a holding part and the other region comprising a sample-carrying part, said holding part being mounted essentially in the area of one end of the tube, the sample-carrying part protruding into the interior of the tube and being supported only by said holding part, said holding part holding said platform non-rotatable with respect to said graphite tube and including means axially engaging said tube to axially position said sample-carrying part in said graphite tube.

2. The apparatus of claim 1, wherein the holding part and the sample-carrying part comprise pyrographite, glass carbon, coated electrographite or high melting metals, such as Ta and W.

3. The apparatus of claim 1, wherein the sample-carrying part has a depression for holding the sample.

4. The apparatus of claim 1, wherein the holding part and the sample-carrying part are connected only via a narrow cross member.

5. In an apparatus for electrothermal atomization comprising a platform serving as a sample carrier and mounted in a graphite tube, the improvement wherein the platform is divided into two functional regions which are adjacent one another in the axial direction, one of said regions comprising a holding part and the other region comprising a sample-carrying part, said holding part being mounted essentially in the area of one end of the tube, the sample-carrying part protruding into the interior of the tube and being supported only by said holding part, said holding part comprising the broader and the sample-carrying part comprises the narrower section of a T-shape, said a broader section being pushed into a pair of slits lying in a common plane at one end of the graphite tube so as to form a good and flush seal.

6. In an apparatus for electrothermal atomization comprising a platform serving as a sample carrier and mounted in a graphite tube, the improvement wherein the platform is divided into two functional regions which are adjacent one another in the axial direction, one of said regions comprising a holding part and the other region comprising a sample-carrying part, said holding part being mounted essentially in the area of one end of the tube, the sample-carrying part protruding into the interior of the tube and being supported only by said holding part and wherein, for the guidance and mounting of the holding part, a radially symmetrical cross member is provided in the area of one end of the tube in the interior of the tube, the cross member having grooves which lie in a plane and through which the holding part is pushed.

7. The apparatus of claim of claim 6, wherein the holding part is provided with at least one stop, which acts against the cross member.

* * * * *